United States Patent

Barnish et al.

[11] Patent Number: 5,362,902
[45] Date of Patent: Nov. 8, 1994

[54] N-(1-(2-CARBOXYETHYL35CLOALKYLCARBONYL)-BETA-ALANINE DERIVATIVES FOR PHARMACEUTICAL USE

[75] Inventors: Ian T. Barnish, Ramsgate; Keith James, Deal, both of England

[73] Assignee: Pfizer Inc., New York, N.Y.

[21] Appl. No.: 910,331

[22] PCT Filed: Nov. 15, 1990

[86] PCT No.: PCT/EP90/01916
§ 371 Date: Jul. 21, 1992
§ 102(e) Date: Jul. 21, 1992

[87] PCT Pub. No.: WO91/08195
PCT Pub. Date: Jun. 13, 1991

[30] Foreign Application Priority Data

Nov. 23, 1989 [GB] United Kingdom ............... 8926512

[51] Int. Cl.$^5$ ............... C07C 311/05; C07C 311/06; A61K 31/215
[52] U.S. Cl. ............... 560/13; 560/25; 560/27; 560/39; 560/41; 562/430; 562/444; 562/450
[58] Field of Search ............... 514/530, 562, 563; 560/13, 39, 41, 25, 27; 562/430, 444, 450

[56] References Cited

U.S. PATENT DOCUMENTS

| | | | |
|---|---|---|---|
| 3,200,150 | 8/1965 | Pollard et al. | 564/138 |
| 3,468,919 | 9/1969 | Kilsheimer et al. | 564/138 |
| 3,941,783 | 3/1976 | Grega et al. | 564/138 |
| 3,975,434 | 8/1976 | Bulteau et al. | 564/139 |
| 4,024,280 | 5/1977 | Murai et al. | 564/138 |
| 4,041,077 | 8/1977 | Ghosez et al. | 564/138 |
| 4,960,792 | 10/1990 | Danilewicz et al. | 514/481 |
| 4,975,444 | 12/1990 | Danilewicz et al. | 514/354 |

FOREIGN PATENT DOCUMENTS 0358398 3/1990 European Pat. Off. ............ 562/430

OTHER PUBLICATIONS

Danilewicz et al, *Biochem. Biophys. Res. Comm.*, 164(1), pp. 58–65 (1989).
Streitwieser & Heathcock, *Introduction to Organic Chemistry*, MacMillan (New York), p. 835 (1976).
March, *Advanced Organic Chemistry*, 3rd ed., John Wiley & Sons (New York), p. 21 (1985).

*Primary Examiner*—Jose G. Dees
*Assistant Examiner*—B. Frazier
*Attorney, Agent, or Firm*—Peter C. Richardson; Paul H. Ginsburg

[57] ABSTRACT

Compounds of formula (I) are diuretic agents for treating various cardiovascular diseases including hypertension, heart failure and renal insufficiency.

15 Claims, No Drawings

N-(1-(2-CARBOXYETHYL35CLOALKYLCAR-BONYL)-BETA-ALANINE DERIVATIVES FOR PHARMACEUTICAL USE

BACKGROUND OF THE INVENTION

This invention relates to a series of cycloalkyl-substituted glutaramide derivatives which are diuretic agents having utility in a variety of therapeutic areas including the treatment of various cardiovascular disorders such as hypertension, heart failure and renal insufficiency.

According to the specification of our European patent application EP-A-0274234 and our pending European patent application No 893051305, we describe and claim certain cycloalkyl-substituted glutaramide derivatives having an aminocycloalkanecarboxylate ring as diuretic agents. The present invention provides further related compounds in which the aminocycloalkanecarboxylate ring is replaced by a beta-alanine group or derivative thereof.

The compounds are inhibitors of the zinc-dependent, neutral endopeptidase E.C.3.4.24.11. This enzyme is involved in the breakdown of several peptide hormones, including atrial natriuretic factor (ANF), which is secreted by the heart and which has potent vasodilatory, diuretic and natriuretic activity. Thus, the compounds of the invention, by inhibiting the neutral endopeptidase E.C.3.4.24.11, can potentiate the biological effects of ANF, and in particular the compounds are diuretic agents having utility in the treatment of a number of disorders, including hypertension, heart failure, angina, renal insufficiency, premenstrual syndrome, cyclical oedema, Menieres disease, hyperaldosteronism (primary and secondary), pulmonary oedema, ascites, and hypercalciuria. In addition, because of their ability to potentiate the effects of ANF the compounds have utility in the treatment of glaucoma. As a further result of their ability to inhibit the neutral endopeptidase E.C.3.4.24.11, the compounds of the invention may have activity in other therapeutic areas including for example the treatment of asthma, inflammation, pain, epilepsy, affective disorders, dementia and geriatric confusion, obesity and gastrointestinal disorders (especially diarrhoea and irritable bowel syndrome), the modulation of gastric acid secretion and the treatment of hyperreninaemia and leukaemia.

SUMMARY OF THE INVENTION

The compounds of the present invention are of the formula:

$$RO_2C-CH(CH_2-)-C(A)(R^1)-C(=O)-NH-C(R^3)(H)-C(R^{18})(R^{19})-CO_2R^4$$
with $R^5-C(H)-$ and $R^2$ substituents wherein A completes a 4 to 7 membered carbocyclic ring which may be saturated or mono-unsaturated and which may optionally be fused to a further saturated or unsaturated 5 or 6 membered carbocyclic ring;

each of R and $R^4$ is independently H, $C_1-C_6$ alkyl, benzyl or an alternative biolabile ester-forming group;

$R^1$ is H or $C_1-C_4$ alkyl;

$R^2$, $R^3$, $R^{18}$ and $R^{19}$ are independently selected from H, $C_1-C_6$ alkyl, $C_1-C_6$ alkoxy, aryl($C_1-C_6$)alkyl, aryl($C_2-C_6$)alkenyl, aryl($C_1-C_4$)alkoxy($C_1-C_4$)alkyl, and hydroxy($C_1-C_4$)alkyl, or $R^3$ and $R^{19}$ are as defined above and $R^2$ and $R^{18}$, together with the carbon atom to which they are attached, form a 2-indanylidene group; and $R^5$ is $C_1-C_6$ alkyl, $C_2-C_6$ alkenyl, $C_2-C_6$ alkynyl, $C_3-C_7$ cycloalkyl, or $C_7$ cycloalkenyl, or $R^5$ is $C_1-C_6$ alkyl substituted by halo, hydroxy, $C_1-C_6$ alkoxy, $C_1-C_6$ alkoxy($C_1-C_6$)alkoxy, $C_3-C_7$ cycloalkyl, $C_7$ cycloalkenyl, aryl, aryloxy, heterocyclyl, $-NR^6R^7$, $-NR^8COR^9$, $-NR^8SO_2R^{10}$, $-CONR^6R^7$ or $R^6R^7N-(C_1-C_6)$alkoxy; or $R^5$ is $C_1-C_6$ alkyl substituted by a group of the formula:

$$-NH^{11}CO-\underset{R^{14}}{\overset{R^{12}}{\underset{|}{\overset{|}{C}}}}-R^{13},$$

$$-NH^{11}SO_2-\underset{R^{14}}{\overset{R^{12}}{\underset{|}{\overset{|}{C}}}}-R^{13} \text{ or}$$

$$-CONR^{11}-\underset{R^{15}}{\overset{R^{13}}{\underset{|}{\overset{|}{C}}}}-R^{14}$$

wherein $R^6$ and $R^7$ are each independently H, $C_1-C_4$ alkyl, $C_3-C_7$ cycloalkyl, aryl, aryl($C_1-C_4$)alkyl, $C_2-C_6$ alkoxyalkyl, or heterocyclyl; or the two groups $R^6$ and $R^7$ are taken together with the nitrogen to which they are attached to form a pyrrolidinyl, piperidino, morpholino, piperazinyl or N—($C_1-C_4$)alkyl-piperazinyl group; or $R^5$ is a biolabile mono or di-ester derivative of S-lysylaminomethyl, $N^2$-acetyl acetyl-S-lysylaminomethyl or $N^2$-methanesulphonyl-S-lysylaminomethyl;

$R^8$ is H or $C_1-C_4$ alkyl;

$R^9$ is $C_1-C_4$ alkyl, $CF_3$, aryl, aryl($C_1-C_4$)alkyl, aryl($C_1-C_4$)alkoxy, heterocyclyl, $C_1-C_4$ alkoxy or $NR^6R^7$ wherein $R^6$ and $R^7$ are as previously defined;

$R^{10}$ is $C_1-C_4$ alkyl, $C_3-C_7$ cycloalkyl, aryl or heterocyclyl;

$R^{11}$ is H, $C_1-C_6$ alkyl, aryl or $C_3-C_7$ cycloalkyl, $R^{12}$ is $R^{11}CONR^{11}-$, $R^{11}SO_2NR^{11}-$, $R^{16}R^{17}N-(CH_2)_p-$, or $R^{11}O-$, wherein each $R^{11}$ is as previously defined above;

$R^{13}$ and $R^{14}$ are each independently H or $C_1-C_6$ alkyl; or $R^{13}$ is H and $R^{14}$ is $C_1-C_6$ alkyl which is substituted by OH, $C_1-C_4$ alkoxy, SH, $SCH_3$, $NH_2$, aryl($C_1-C_6$)alkyl—OCONH—, $NH_2CO$—, $CO_2H$, guanidino, aryl, or heterocyclyl; or the two groups $R^{13}$ and $R^{14}$ are joined together to form, with the carbon atom to which they are attached, a 5 or 6 membered carbocyclic ring which may be saturated or mono-substituted and which may optionally be substituted by $C_1$–$C_4$ alkyl or fused to a further 5 or 6 membered saturated or unsaturated carbocyclic ring; or $R^{13}$ is H, and $R^{12}$ and $R^{14}$ are linked to form a 2—(-N—COR$^{11}$-4-aminopyrrolidinyl) group;

$R^{15}$ is $R^{16}R^{17}$NCO—, $R^{11}$OCO—, $R^{11}$OCH$_2$— or heterocyclyl, wherein $R^{11}$ is as previously defined above;

$R^{16}$ and $R^{17}$ are each independently H or $C_1$–$C_6$ alkyl, and p is 0 or an integer of from 1 to 6; and pharmaceutically acceptable salts thereof and bioprecursors therefor.

In the above definitions, unless otherwise indicated, alkyl groups having three or more carbon atoms may be straight or branched-chain. The term aryl as used herein means an aromatic hydrocarbon group such as phenyl, naphthyl or biphenyl which may optionally be substituted with one or more OH, CN, CF$_3$, $C_1$–$C_4$ alkyl, $C_1$–$C_4$ alkoxy groups or halo atoms. Halo means fluoro, chloro, bromo or iodo.

The term heterocyclyl means a 5 or 6 membered nitrogen, oxygen or sulphur containing heterocyclic group which, unless otherwise stated, may be saturated or unsaturated and which may optionally include a further oxygen or one to three nitrogen atoms in the ring and which may optionally be benzofused or substituted with for example, one or more halo, $C_1$–$C_4$ alkyl, hydroxy, carbamoyl, benzyl, oxo, amino or mono or di-($C_1$–$C_4$ alkyl)amino or ($C_1$–$C_4$ alkanoyl)amino groups. Particular examples of heterocycles include pyridyl, pyrazinyl, pyrimidinyl, pyridazinyl, pyrrolyl, imidazolyl, pyrazolyl, triazolyl, tetrazolyl, furanyl, tetrahydrofuranyl, tetrahydropyranyl, dioxanyl, thienyl, oxazolyl, isoxazolyl, thiazolyl, indolyl, isoindolinyl, quinolyl, quinoxalinyl, quinazolinyl and benzimidazolyl, each being optionally substituted as previously defined.

The compounds of formula (I) may contain several asymmetric centres and thus they can exist as enantiomers and diastereoisomers. The invention includes both mixtures and the separated individual isomers. The substituents $R^2$, $R^{18}$ and $R^3$, $R^{19}$ respectively may be of threo or erythro configuration relative to each other. As the carbon atom to which $R^5$ is attached constitutes a chiral centre, the compounds may exist as R or S forms with respect to this centre. The terms erythro and threo are as defined in the article by D-C Ha, D. J. Hart and T-K Yang. J. Am. Chem. Soc. 1984 106 4819.

The pharmaceutically acceptable salts of the compounds of formula (I) containing an acidic centre are those formed with bases which form non-toxic salts. Examples include the alkali metal salts such as the sodium, potassium or calcium salts or salts with amines such as diethylamine. Compounds having a basic centre can also form acid addition salts with pharmaceutically acceptable acids. Examples include the hydrochloride hydrobromide, sulphate or bisulphate, phosphate or hydrogen phosphate, acetate, citrate, fumarate, fluconate, lactate, maleate, succinate and tartrate salts.

The term bioprecursors in the above definition means a pharmaceutically acceptable biologically degradable derivative of the compound of formula (I) which, upon administration to an animal or human being, is converted in the body to produce a compound of the formula (I).

A preferred group of compounds are those in which A is (CH$_2$)$_4$ and $R^1$ is H, A thus completing a cyclopentane ring.

Examples of $R^2$, $R^3$, $R^{18}$ and $R^{19}$ are H, styryl, methyl, ethyl, isopropyl and methoxy. In a preferred group of compounds $R^2$ is aryl($C_2$–$C_6$)alkenyl, such as styryl, $R^{18}$ is H and either $R^3$ and $R^{19}$ are both methyl or one of $R^3$ and $R^{19}$ is hydrogen and the other is methyl, methoxy or isopropyl. When one each of $R^2$, $R^{18}$ and $R^3$, $R^{19}$ is H and the other is a substituent other than H, these substituents are preferably in the erythro configuration relative to each other.

Also preferred are those compounds of formula (I) wherein R and $R^4$ are both H (diacids) as well as biolabile mono and di-ester derivatives thereof wherein one or both of R and $R^4$ is a biolabile ester-forming group.

The term biolabile ester-forming group is well understood in the art as meaning a group which provides an ester which can be readily cleaved in the body to liberate the corresponding diacid of formula (I) wherein R and $R^4$ are both H. A number of such ester groups are well known, for example in the penicillin area of in the case of the ACE-inhibitor antihypertensive agents.

In the case of the compounds of formula (I) such biolabile pro-drug esters are particularly advantageous in providing compounds suitable for oral administration. The suitability of any particular ester-forming group can be assessed by conventional animal or in vitro enzyme hydrolysis studies. Thus, desirably for optimum effect, the ester should only be hydrolysed after absorption; accordingly, the ester should be resistant to hydrolysis before absorption by digestive enzymes but should be readily hydrolysed by, for example, liver enzymes. In this way the active diacid is released into the bloodstream following oral absorption.

In addition to lower alkyl esters (particularly ethyl) and benzyl esters, suitable biolabile esters include alkanoyloxyalkyl esters, including alkyl, cycloalkyl and aryl substituted derivatives thereof, aryloxyalkyl esters, aroyloxyalkyl esters, aralkyloxyalkyl esters, arylesters, aralkylesters, and haloalkyl esters wherein said alkanoyl or alkyl groups have from 1 to 8 carbon atoms and are branched or straight chain and said aryl groups are phenyl, naphthyl or indanyl optionally substituted with one or more $C_1$–$C_4$ alkyl or $C_1$–$C_4$ alkoxy groups or halo atoms.

Thus examples of R and $R^4$ when they are biolabile ester-forming groups other than ethyl and benzyl include: 1-(2,2-diethylbutyryloxy)ethyl, 2-ethylpropionyloxymethyl, 1-(2-ethylpropionyloxy)ethyl, 1-(2,4-dimethylbenzoyloxy)ethyl, 1-(benzoyloxy)benzyl, 1-(benzoyloxy)ethyl, 2-methyl-1-propionyloxypropyl, 2,4,6-trimethylbenzoyloxymethyl, 1-(2,4,6-trimethylbenzoyloxy)ethyl, pivaloyloxymethyl, phenethyl, phenpropyl, 2,2,2-trifluoroethyl, 1- or 2-naphthyl, 2,4-dimethylphenyl, 4-t-butylphenyl, 5-(4-methyl-1,3-dioxalynyl-2-onyl)methyl and 5-indanyl.

Compounds of the formula (I) wherein one or both of R and $R^4$ are $C_1$–$C_6$ alkyl, particularly ethyl, t-butyl or benzyl, are valuable intermediates for the preparation of the diacids wherein R and $R^4$ are both H.

In a further preferred group of compounds $R^5$ is methylene substituted by a group of the formula —NHCOCR$^{12}$R$^{13}$R$^{14}$, particularly where $R^{12}$ is NH$_2$, $R^{11}$CONH— or $R^{11}$SO$_2$NH—, $R^{13}$ is H and $R^{14}$ is —(CH$_2$)$_4$NH$_2$. Particularly preferred are such groups derived from S-lysine, thus especially preferred $R^5$ substituents of this type include N²-acetyl-S-lysylaminomethyl, N²-methanesulphonyl-S-lysylaminomethyl, N²-phenylsulphonyl-S-lysylaminomethyl N²-cyclobutylcarbonyl-S-lysylaminomethyl, N²-t-butoxycarbonyl-S-lysylaminomethyl and S-lysyl-aminomethyl.

In a further group of preferred compounds $R^5$ is $C_1$-$C_6$ alkyl substituted by $C_1$-$C_6$ alkoxy, particularly methoxyethyl; or wherein $R^5$ is $C_1$-$C_6$ alkyl substituted by $C_1$-$C_6$ alkoxy ($C_2$-$C_6$) alkoxy, particularly 2-methoxyethoxymethyl.

Particularly preferred compounds are those in which R, $R^1$ and $R^4$ are H, A is $(CH_2)_4$, $R^2$ is styryl, $R^3$ is methyl, $R^2$ and $R^3$ being in the erythro relative configuration, $R^{18}$ and $R^{19}$ are H, and $R^5$ is S-lysylaminomethyl, N²-acetyl-S-lysylaminomethyl and N²-methanesulphonyl-S-lysylamino-methyl and biolabile ester derivatives thereof. These compounds may exist in the R- or S-forms, or a mixture thereof, relative to the chiral centre to which $R^5$ is attached. In the case of the N²-methanesulphonyl-S-lysylaminomethyl derivative, the S-form is preferred.

DETAILED DESCRIPTION OF THE INVENTION

The compounds of formula (I) may be prepared by a number of different processes. The basic procedure involves the synthesis of a partially protected geminally disubstituted glutaric acid derivative which is coupled to an amine to give the desired glutaramide. The carboxylic acid group in the amine, if free, or any reactive groups in $R^5$, may require protection during the coupling step and such protecting groups are removed in the final stage of the process.

The synthetic route is illustrated in Scheme 1 wherein A, $R^1$, $R^2$, $R^3$, $R^{18}$ and $R^{19}$ are as previously defined, $R^{5'}$ is as defined for $R^5$ with any reactive group therein protected if necessary and $R^{20}$ and $R^{21}$ are as defined for R and $R^4$ excluding H, or they are conventional carboxylic acid protecting groups:

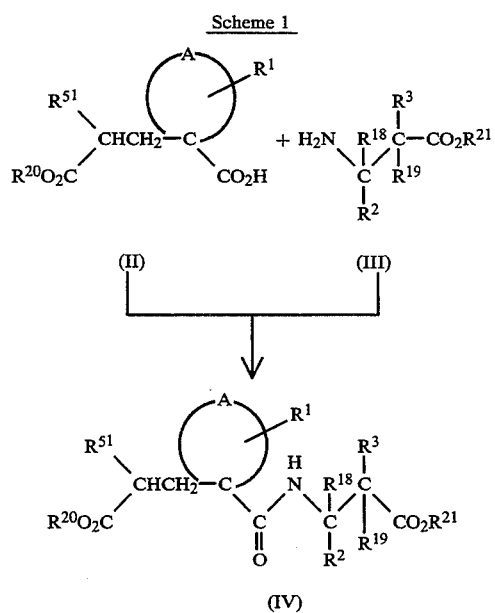

Scheme 1

The reaction of the compounds of formula (II) and (III) is achieved using conventional amide coupling techniques. Thus in one process the reaction is achieved with the reactants dissolved in an organic solvent, e.g. dichloromethane, using a diimide condensing agent, for example 1-ethyl-3-(dimethylaminopropyl)-carbodiimide, or N,N'-dicyclohexylcarbodiimide, advantageously in the presence of 1-hydroxybenzotriazole and an organic base such as 4-methylmorpholine. The reaction is generally complete after a period of from 12 to 24 hours at room temperature and the product is then isolated by conventional procedures, i.e. by washing with water or filtration to remove the urea by-product and evaporation of the solvent. The product may be further purified by crystallisation or chromatography, if necessary. The compounds of formula (IV) include compounds of formula (I) wherein R and $R^4$ are $C_1$-$C_6$ alkyl or benzyl.

In some cases the coupled product, in protected form, may be subjected to conventional chemical transformation reactions to allow preparation of further compounds of formula (IV). Thus for example compounds of formula (IV) wherein $R^{5'}$ contains an ester group may be hydrolysed or hydrogenated to generate the carboxylic acid which may be further reacted, for example with an amine, to give amide derivatives.

Similarly compounds wherein $R^{5'}$ contains a substituted or protected amino group (for example a benzylamino, dibenzylamino, benzyloxycarbonylamino or t-butyloxycarbonylamino group) may be converted to the free amines by, for example, hydrogenation or hydrolysis as appropriate. The amines produced may be further reacted; thus for example reaction with a sulphonyl halide yields the corresponding sulphonamides, acylation with an acid chloride or anhydride yields the corresponding amides, reaction with an isocyanate yields urea derivatives and reaction with a chloroformate yields the carbamate respectively. All these transformations are entirely conventional and appropriate conditions and reagents for their performance will be well known to those skilled in the art as will other variations and possibilities.

The diesters of formula (IV) may be further reacted to give the monoester of diacid derivatives of formula (I) wherein one or both of R and $R^4$ are H. The conditions used will depend on the precise nature of the groups $R^{20}$ and $R^{21}$ present in the compound of formula (IV) and a number of variations are possible. Thus for example when both of $R^{20}$ and $R^{21}$ are benzyl, hydrogenation of the product will yield the diacid or formula (I) wherein R and $R^4$ are both H. Alternatively if one of $R^{20}$ and $R^{21}$ is benzyl and the other is alkyl, hydrogenation will yield a monoester product. This can be hydrolysed, if desired, to again yield the diacid product. When one of $R^{20}$ and $R^{21}$ is t-butyl, treatment of the compound of formula (IV) with trifluoroacetic acid yields the corresponding monoacid. The diester product wherein $R^{20}$ and $R^{21}$ are benzyl or lower alkyl can also be treated with trimethylsilyl iodide to produce the dicarboxylic acid product. If some other carboxylic acid protecting group is used for $R^{20}$ or $R^{21}$ then clearly appropriate conditions for its removal must be employed in the final step to give the ester or diacid product of formula (I). In the case where the ring A or the substituent $R^2$ or $R^5$ is unsaturated, the deprotection must be effected by non-reductive methods, thus for example if either of R and $R^4$ is benzyl, they may be removed by treatment with trimethylsilyl iodide.

As well as removing any protecting group which may be present in $R^{5'}$, a number of chemical transformation reactions are possible on the final mono-ester or diacid products as previously described. In each case the product may be obtained as the free carboxylic acid or it may be neutralised with an appropriate base and isolated in salt form.

In a variant of the above procedure, compounds of the formula (I) wherein $R^5$ is $C_1$-$C_6$ alkyl substituted by $-NR^8COR^9$, $-NR^8SO_2R^{10}$, $-NR^{11}COCR^{12}R^{13}R^{14}$ or $-NR^{11}SO_2CR^{12}R^{13}R^{14}$ are prepared by a process which involves acylating or sulphonylating a compound of the formula:

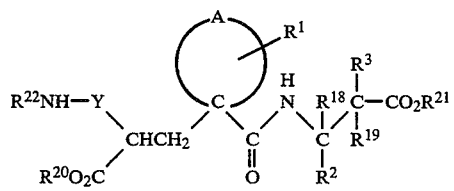

(V)

wherein $R^{22}$ is as defined for $R^8$ or $R^{11}$, $R^{20}$ and $R^{21}$ are as previously defined and Y is a $C_1$-$C_6$ alkyl group; by reaction with an acid of the formula $R^9CO_2H$, $R^{10}SO_3H$, $R^{12}R^{13}R^{14}COO_2H$, or $R^{12}R^{13}R^{14}CSO_3H$, or an activated derivative thereof. The resulting amide or sulphonamide product is then deprotected if required and the diester product hydrolysed to yield the carboxylic acids of formula (I) wherein R and $R^4$ are each H as previously described.

The compounds of formula (V) are prepared following the procedures shown in Scheme 1 but using a compound of formula (II) having $R^{5'}$ as a protected amine derivative. Thus, for example $R^{5'}$ can contain a bis-[(1S)-phenylethyl]aminomethyl substituent. Hydrogenation of the coupled product gives the corresponding free amine of formula (IV) wherein $R^{22}$ is H and Y is $CH_2$. This route is of particular value for the preparation of compounds having 2(S) stereochemistry in the glutaramide backbone.

The starting spiro-substituted glutaric acid mono esters of formula (II) may be prepared as described in our European patent applications EP-A-0274234 and 89305180.5.

The amines of formula (III) are generally novel compounds (particularly when the substituents have defined stereochemistry) and they are prepared by appropriate synthetic procedures in accordance with literature procedents. In one procedure, following the method of D. J. Hart, K. Kanai, D. G. Thomas and T-K. Yang, J. Org. Chem. 1983, 48, 289, the appropriate substituted ethyl propanoate is treated with n-butyl lithium in the presence of diisopropylamine and the product treated with the appropriate N-(trimethylsilyl)imine, followed by acid hydrolysis to yield the desired amine. The N-(trimethylsilyl)imine may be obtained by reaction of the appropriate aldehyde with lithium bis(trimethylsilyl)amide. These procedures are illustrated in the Preparations given hereafter.

Appropriate coupling and protecting methods for all of the above steps and alternative variations and procedures will be well known to those skilled in the art by reference to standard test books and to the examples provided hereafter.

As previously mentioned, the compounds of the invention are potent inhibitors of the neutral endopeptidase (E.C.3.4.24.11). This enzyme is involved in the breakdown of a number of peptide hormones and, in particular, it is involved in the breakdown of atrial natriuretic factor (ANF). This hormone consists of a family of related natriuretic peptides, secreted by the heart, of which the major circulating form in humans is known to be the 28 amino-acid peptide referred to as -hANP. Thus, by preventing the degradation of ANF, by endopeptidase E.C.3.4.24.11, the compounds of the invention can potentiate its biological effects and the compounds are thus diuretic and natriuretic agents of utility in a number of disorders as previously described.

Activity against neutral endopeptidase E.C.3.4.24.11 is assessed using a procedure based on the assay described by J. T. Gafford, R. A. Skidgel, E. G. Erdos and L. B. Hersh, *Biochemistry*, 1983, 32, 3265-3271. The method involves determining the concentration of compound required to reduce by 50% the rate of release of radiolabelled hippuric acid from hippuryl-L-phenylalanyl-L-arginine by a neutral endopeptidase preparation from rat kidney.

The activity of the compounds as diruetic agents is determined by measuring their ability to increase urine output and sodium ion excretion in saline loaded conscious mice. In this test, male mice (Charles River CD1, 22-28 g) are acclimatised and starved overnight in metabowls. The mice are dosed intravenously via the tail vein, with the test compound dissolved in a volume of saline solution equivalent to 2.5% of body weight. Urine samples are collected each hour for two hours in pre-weighted tubes and analysed for electrolyte concentration. Urine volume and sodium ion concentration from the test animals are compared to a control group which received only saline.

For administration to man in the curative or prophylactic treatment of hypertension, congestive heart failure or renal insufficiency, oral dosages of the compounds will generally be in the range of from 4-800 mg daily for an average adult patient (70 kg). Thus for a typical adult patient, individual tablets or capsules contain from 2 to 400 mg of active compound, in a suitable pharmaceutically acceptable vehicle or carrier for administration singly, or in multiple doses, once or several times a day. Dosages for intravenous administration would typically be within the range 1 to 400 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously intramuscularly or subcutaneously. For parenteral administration, they are best used in the form of a sterile aqueous solution which may contain other substances, for example, enough salts or glucose to make the solution isotonic with blood.

The compounds may be administered alone but may also be administered together with such other agents as the physician shall direct to optimise control of blood pressure or to treat congestive heart failure, renal insufficiency or other disorders in any particular patient in accordance with established medical practice. Thus the compounds can be co-administered with a variety of cardiovascular agents, for example with an ACE inhibitor such as captopril or enalapril to facilitate the control of blood pressure in treatment of hypertension; or with digitalis, or another cardiac stimulant, or with an ACE inhibitor, for the treatment of congestive heart failure. Other possibilities include co-administration with a calcium antagonist (e.g. nifedipine, amlodopine or diltiazem) a beta-blocker (e.g. atenolol) or an alpha-blocker (e.g. proasin or dixazosin) as shall be determined by the physician as appropriate for the treatment of the particular patient or condition involved.

In addition to the above, the compounds may also be administered in conjunction with exogenous ANF, or a derivative thereof or related peptide or peptide fragment having diuretic/natriuretic activity or with other ANF-gene related peptides (e.g. as described by D. L. Vesely et al, Biochem. Biophys. Res. Comm., 1987, 143, 186).

Thus in a further aspect the invention provides a pharmaceutical composition comprising a compound of the formula (I), or a pharmaceutically acceptable salt thereof or bioprecursor therefor, together with a pharmaceutically acceptable diluent or carrier.

The invention also includes a compound of the formula (I), or a pharmaceutically acceptable salt thereof or bioprecursor therefor, for use in medicine, particularly for use as a diuretic agent for the treatment of hypertension, congestive heart failure or renal insufficiency in a human being.

The invention further includes the use of a compound of the formula (I) for the manufacture of a medicament for the treatment of hypertension, heart failure, angina, renal insufficiency, premenstrual syndrome, cyclical oedema, Menieres disease, hyperaldosteronism, pulmonary oedema, ascites, hypercalciuria, glaucoma, asthma, inflammation, pain, epilepsy, affective disorders, dementia and geriatric confusion, hyperreninaemia, leukaemia, and the modulation of gastric acid secretion.

The preparation of the compounds of the invention will now be more particularly illustrated by reference to the following experimental examples, in which EXAMPLES 1–30 describe preparation of compounds of the formula (I) and Preparations 1–12 describe preparations of starting amines of formula III. The purity of compounds was routinely monitored by thin layer chromatography using Merck Kieselgel 60 $F_{254}$ plates. $^1$H-Nuclear magnetic resonance spectra were recorded using a Nicolet QE-300 spectrometer and were in all cases consistent with the proposed structures.

EXAMPLE 1

2(R,S)-(N$^6$-t-Butoxycarbonyl-N$^2$-methanesulphonyl-S-lysylaminomethyl)-3-[1-(1-carboxycyclopentyl)]-propanoic acid t-butyl ester (a) 4-Methylmorpholine salt of 2(R,S)aminomethyl-3-(1-carboxycyclopentyl)propanoic acid t-butyl ester A stirred mixture of 2 (R,S)-Dibenzylaminomethyl-3-(1-carboxycyclopentyl)propanoic acid t-butyl ester hydrochloride (1.46 g, 3 mmol) and 4-methylmorpholine (3 ml) in ethanol (30 ml) was hydrogenated over palladium (from 20% Pd(OH)$_2$/C: 2.0 g) at 60 psi (4.1 bar).

After 18 hours the mixture was filtered through Arbicel, the solvent evaporated and the residue dried azeotropically with toluene. The required primary amino acid 4-methylmorpholine salt containing one mole equivalent of 4-methylmorpholine hydrochloride was obtained.

(b) 2(R,S)-N$^6$-t-Butoxycarbonyl-N$^2$-methanesulphonyl-S-lysylaminomethyl)-3-[1-(1-carboxycyclopentyl)]-propanoic acid t-butyl ester 1-(3-Dimethylaminopropyl)-3-ethylcarbodiimide hydrochloride (0.57 g, 3 mmol) was added to a stirred mixture of N$^6$-t-butoxycarbonyl-N$^2$-methanesulphonyl-S-lysine (0.97 g, 3 mmol), 1-hydroxybenzotriazole (0.4 g, 3 mmol) and 4-methylmorpholine (0.66 ml, 6 mmol) in dry dichloromethane (20 ml). After 0.5 hours, the resulting solution was added to the crude salt described above and the reaction mixture stirred for 16 hours at room temperature, then evaporated under vacuum. The residue was dissolved in ethyl acetate (25 ml) and the solution washed successively with 1M hydrochloric acid (2×2 ml), saturated aqueous solution bicarbonate solution (2×10 ml), water (20 ml) and saturated brine (20 ml), then dried (MgSO$_4$) and evaporated under vacuum. The crude material (2.0 g) was purified by chromatography on silica gel using an ethyl acetate-methanol-diethylamine elution gradient (99:1:1–90:10:1) to afford the required product (0.68 g). Rf 0.35 (silica; ethyl acetate-methanol-isopropyl-amine/80:20:1).

EXAMPLES 2–4

The compounds of Table 1 were obtained by the general method of Example I, using the appropriate S-lysine derivative. Compound 4, the S,S-enantiomer of the compound of Example 1, was synthsised in analgous fashion from the sodium salt of 2(S)-aminomethyl-3-(1-carboxycyclopentyl)propanoic acid t-butyl ester, described in EP 89308740.3.

TABLE 1

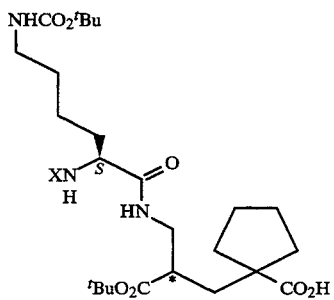

| | | | Analysis % (theoretical in brackets) or TLC (thin layer chromatography) data | | |
|---|---|---|---|---|---|
| Example | X | * | C | H | N |
| 2 | CO$_2^t$Bu | R, S | Rf 0.47 and 0.54 (silica; EtOAc—MeOH—$^i$PrNH$_2$/80:20:1) | | |
| 3 | COMe | R, S | 59.27 | 8.81 | 7.72 |
| | | | (59.37 | 8.77 | 7.69) |
| 4 | SO$_2$Me | S | 54.71 | 8.08 | 7.66 |
| | | | (54.06 | 8.20 | 7.27) |

EXAMPLE 5

N-{1-[2(R,S)-Benzyloxycarbonylpentyl]cyclopentylcarbonyl}-erythro-2-methyl-3-styryl-β-alanine, methyl ester 1-(3-Dimethylaminopropyl)-3-ethylcarbodiimide hydrochloride (1.73 g, 9.2 mmol) was added to a stirred mixture of 1-[2-(R,S)-benzyloxycarbonylpentyl]cyclopentane carboxylic acid (EP 0274234, Example 13) (1.46 g, 4.6 mmol), 1-hydroxybenzotriazole (0.62 g, 4.6 mmol), erythro-2-methyl-3-styryl-β-alanine, methyl ester (1.0 g, 4.6 mmol) and 4-methylmorpholine (1.0 ml, 9.2 mmol) in dry dichloromethane (50 ml). After 16 hours at room temperature, the reaction solution was evaporated under vacuum and the residue dissolved in ethyl acetate (50 ml). This solution was washed successively with 1M hydrochloric acid (2×25 ml), saturated aqueous sodium bicarbonate solution (2×25 ml), water (25 ml) and saturated brine (25 ml), then dried (MgSO$_4$) and evaporated under vacuum. The crude material was purified by chromatography on silica gel using a dichloromethane-hexane elution gradient (1:2–2:1) to provide the required product as a colourless oil (1.7 g). Found: C,73.92; H,8.14; N,2.86. $C_{32}H_{41}NO_5$ requires C,73.96; H,7.85; N,2.70%.

EXAMPLES 6–15

The compounds of Table 2 were obtained by the general method of Example 5 from the appropriate 1-substituted cyclopentane carboxylic acids and β-alanine ester derivatives.

TABLE 2

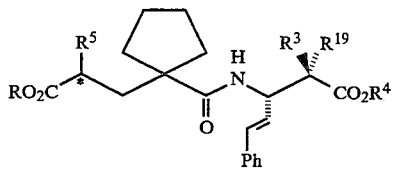

| Compound | R | $R^5$ | * | $R^3$ | $R^{19}$ | $R^4$ | C | H | N |
|---|---|---|---|---|---|---|---|---|---|
| 6 | $^tBu$ | $CH_2OCH_2CH_2OMe$ | R, S | Me | H | Me | 68.28 (67.77 | 8.42 8.53 | 2.95 2.63) |
| 7 | $CH_2Ph$ | $CH_2CH_2Me$ | R, S | $CHMe_2$ | H | Me | 73.08 (73.35 | 8.31 8.33 | 2.88 2.52) (a) |
| 8 | $CH_2Ph$ | $CH_2CH_2Me$ | R, S | H | OMe | Me | 71.35 (71.75 | 7.68 7.72 | 2.91 2.62) |
| 9 | $CH_2Ph$ | $CH_2CH_2Me$ | R, S | OMe | H | Me | 72.10 (71.75 | 8.10 7.72 | 2.83 2.62) |
| 10 | $CH_2Ph$ | $CH_2CH_2Me$ | R, S | H | H | Me | 70.24 (69.90 | 7.28 7.38 | 3.64 2.63) (b) |
| 11 | $CH_2Ph$ | $CH_2CH_2Me$ | R, S | Me | Me | Me | 73.84 (74.26 | 7.94 8.12 | 2.78 2.62) |
| 12 | $^tBu$ | S<br>CH$_2$NHCOCH(CH$_2$)$_4$NHBOC<br>\|<br>NHBOC | R, S | Me | H | Et | Rf 0.50 (silica; EtOAc-hexane/1:1) | | |
| 13 | $^tBu$ | S<br>CH$_2$NHCOCH(CH$_2$)$_4$NHBOC<br>\|<br>NHCOMe | R, S | Me | H | Et | 64.08 (64.29 | 8.37 8.55 | 7.27 7.32) (a) |
| 14 | $^tBu$ | S<br>CH$_2$NHCOCH(CH$_2$)$_4$NHBOC<br>\|<br>NHSO$_2$Me | R, S | Me | H | Et | 59.74 (59.90 | 8.09 8.17 | 6.92 6.99) (a) |
| 15 | $^tBu$ | S<br>CH$_2$NHCOCH(CH$_2$)$_4$NHBOC<br>\|<br>NHSO$_2$Me | S | Me | H | Et | 60.11 (59.90 | 8.05 8.17 | 6.68 6.99) (a) |

(a) ½H$_2$O
(b) 1¼H$_2$O
BOC = t-Butoxycarbonyl

EXAMPLE 16

N-{1-[2(R,S)-Carboxypentyl]cyclopentylcarbonyl}-erythro-2-methyl-3-styryl-β-alanine A stirred mixture of iodine (6.6 g, 26 mmol) and hexamethyldisilane (4.3 g, 29.3 mmol) was heated at 70° C. under dry nitrogen for 1.5 hours, then diluted with cyclohexene (80 ml). To this mixture was added a solution of the title product of Example 5 (1.7 g, 3.3 mmol) in cyclohexene (50 ml), then the resulting mixture stirred at 75° C. for 4 hours.

The bulk of the cyclohexene was removed under vacuum and the residue partitioned between ether and 1M aqueous sodium hydroxide solution. The aqueous phase was separated, acidified with 2M hydrochloric acid and extracted with ether (2x). Evaporation under vacuum of the combined and dried (MgSO$_4$) ether extracts gave the required product as a beige foam (0.9 g). Found: C,68.56; H,8.17; N,3.26. $C_{24}H_{33}NO_5$: ¼H$_2$O requires C,68.63; H,8.04; N,3.34%.

EXAMPLES 17-21

The compounds of Table 3 were obtained by the general method of Example 16 from the products of Examples 7-11 respectively.

TABLE 3

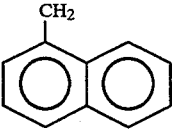

| Compound | R⁵ | R³ | R¹⁹ | Analysis % (theoretical in brackets) | | |
|---|---|---|---|---|---|---|
| | | | | C | H | N |
| 17 | CH₂CH₂Me | CHMe₂ | H | 70.72 (70.40 | 8.50 8.41 | 3.12 3.16) |
| 18 | CH₂CH₂Me | H | OMe | 66.05 (66.11 | 7.68 7.74 | 3.30 3.21) (a) |
| 19 | CH₂CH₂Me | OMe | H | 65.76 (66.11 | 7.73 7.74 | 3.23 3.21) (a) |
| 20 | CH₂CH₂Me | H | H | 68.16 (68.04 | 7.76 7.82 | 3.64 3.45) (a) |
| 21 | CH₂CH₂Me | Me | Me | 68.91 (69.18 | 8.21 8.24 | 3.34 3.23) (a) |

(a) ½H₂O

EXAMPLE 22

N-{1-[2(R,S)-Carboxy-3-(2-methoxyethoxy)propyl]cyclopentylcarbonyl}-erythro-2-methyl-3-styryl-β-alanine Trifluoroacetic acid (4 ml) was added to a stirred solution of the product of Example 6 (0.30 g, 0.56 mmol) in dry dichloromethane (4 ml). After 2 hours at room temperature the reaction mixture was evaporated under vacuum., then most of the residual trifluoroacetic acid removed azeotropically using dichloromethane (3x). The residue was partitioned between ether and water, then the aqueous phase adjusted to pH4 with 1M aqueous ammonium bicarbonate solution and further shaking together of the ether and aqueous phase effected. The ether phase was separated and extracted with 0.5M aqueous sodium hydroxide solution (8 ml), then the aqueous phase separated and allowed to stand at room temperature for 16 hours.

The sodium hydroxide solution was acidified to pH 1 with 1M hydrochloric acid, then extracted with ether (2x). Evaporation under vacuum of the dried (MgSO₄) ether extracts furnished the required product as a colourless oil (0.15 g). Found: C,62.91; N,7.64; N,2.90. C₂₅H₃₅NO₇; H₂O requires C,62.61; H,7.78; N,2.92%.

EXAMPLE 23

N-{1-[2(S)-ᵗbutoxycarbonyl-3-(N²-methanesulphonyl-S-lysylamino)-propyl]cyclopentylcarbonyl}-erythro-2-methyl-3-styryl-β-alanine To a stirred solution of the diester from example 15 (0.39 g, 0.5 mmol) in dioxan (5 ml) at room temperature was added aqueous sodium hydroxide (0.06 mg in 1 ml) and the reaction mixture was stirred overnight at room temperature. The solvent was removed under reduced pressure, and the resulting gum partitioned between ethyl acetate (50 ml) and water (25 ml). The organic phase was washed with water (3×10 ml), dried (MgSO₄), filtered, and evaporated to yield a colourless solid (0.33 g). Chromatography over silica gel (0.5 g) eluting with ethyl acetate/hexane (1:1), adding up to 2% methanol, yielded after combination and evaporation of the appropriate fractions, the title compound as a solid (190 mg). Found: C, 58.85; H, 8.02; N, 7.19%. C₃₈H₆₀N₄O₁₀S requires: C, 58.92; H, 7.95; N, 7.15%.

EXAMPLE 24

N-{1-[2(S)-ᵗbutoxycarbonyl-3-(N²-methanesulphonyl-S-lysylamino)-propyl]cyclopentanecarbonyl}-erythro-2-methyl-3-styryl-β-alanine 1-benzoyloxyethyl ester To a solution of the acid obtained from example 23 (0.5 g, 0.65 mmol) in acetonitrile (5 ml) was added aqueous cesium carbonate (0.106 g in 2 ml) and the solution evaporated to dryness, aceotroped with toluene and taken up in N,N-dimethylacetamide (5 ml). 1-Benzoyloxy ethyl chloride (0.12 g) was added and the reaction mixture stirred at room temperature overnight. A further 0.05 g of the chloride was added and the mixture sonicated for 2 hr (temperature rise to 40° C.). The reaction mixture was evaporated under reduced pressure, partitioned between ethyl acetate (150 ml) and water (20 ml), and acidified with dilute HCl. The organic phase was washed with water, dried (MgSO₄), filtered and evaporated to yield an oil (0.6 g). Chromatography over silica gel (60 g) in hexane/ethyl acetate (2:1) and combination and evaporation of the desired fractions yielded the title compound as an oil (0.32 g, 54%). Found: C, 61.66; H, 7.59; N, 6.04%. C₄₇H₆₈N₄O₁₂S requires: C, 61.82; H, 7.51; N, 6.14%.

EXAMPLES 25-28

The compounds of Table 4 were prepared by the method of Example 24, replacing the 1-benzoyl ethyl chloride with the appropriate chloride.

TABLE 4

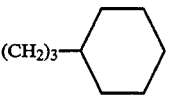

| Example | R | Analysis % (theoretical in brackets) | | |
|---|---|---|---|---|
| | | C | H | N |
| 25 | CH₂-naphthyl | 64.79 (65.02 | 7.28 7.57 | 5.89 6.19) |
| 26 | (CH₂)₃-cyclohexyl | 63.52 (63.49 | 8.70 8.61 | 6.24 6.30) |
| 27 | C₁₁H₂₃ | 64.33 (64.03 | 8.88 8.99 | 6.18 6.10) |

TABLE 4-continued

[Structure: BOCHN-(CH2)-CH(CO2tBu)-CH2-NH-C(=O)-C(NHSO2CH3)(H)- with cyclopentyl-C(=O)-NH-CH(CH=CH-Ph)-CH(Me)-CO2R]

| Example | R | Analysis % (theoretical in brackets) | | |
|---|---|---|---|---|
| | | C | H | N |
| 28 | (CH2)4—O—[naphthyl] | 64.26 (64.84 | 7.43 7.74 | 5.80 5.82) |

EXAMPLE 29

N-{1-[2(S)-*t*butoxycarbonyl-3-(N²-methanesulphonyl-S-lysylamino)-propyl]cyclopentylcarbonyl}-erythro-2-methyl-3-styryl-β-alanine 5-indanyl ester A mixture of the acid obtained from example 23 (0.5 g, 0.65 mmol), 5-indanol (0.22 g, 1.6 mmol), 1-hydroxybenztriazole (0.11 g, 0.72 mmol), N-methylmorpholine (0.08 g, 0.85 mmol) and 1-(3-dimethylamino propyl)-3-ethylcarbodiimide hydrochloride (0.16 g, 0.85 mmol) in methylene chloride (15 ml) was stirred at room temperature for 3 days. The reaction mixture was concentrated by evaporation in vacuo, taken up into ethyl acetate (200 ml), washed with NaHCO3aq (3×40 ml) and brine (40 ml), dried (MgSO4), filtered and evaporated to yield an oil (0.7 g). This was chromatographed over silica gel (14 g) in hexane:ethylacetate (2:1), and after combination of the desired fractions, evaporation yielded the title compound as an oil (0.3 g). Found: C, 63.93; H, 7.70; N, 6.25%. $C_{47}H_{68}N_4O_{10}S$ requires: C, 64.06; H, 7.78; H, 6.36%.

EXAMPLE 30

N-{1-[2(S)-Carboxy-3-(N²-methanesulphonyl-S-lysylamino)-propyl]cyclopentylcarbonyl}-erythro-2-methyl-3-styryl-β-alanine, ethyl ester, hydrochloride A stirred, ice-cold solution of the product from Example 15 (0.95 g, 1.2 mmol) in dry dichloromethane (20 ml) was saturated with dry hydrogen chloride, then the cooling bath removed. After a further 1 hour, the reaction mixture was evaporated under vacuum to afford the required product as a beige foam (0.80 g). Found: C,53.34; H,7.28; N,7.72. $C_{31}H_{48}N_4O_8S$; HCl; ¼ H2O requires C,53.52; H,7.46; N,8.05%.

EXAMPLES 31–33

The compounds of Table 5 were obtained by the general method of Example 30 from the products of Examples 12, 13 and 14 respectively.

TABLE 5

[Structure: NH2-(CH2)-CH(NHY)(S)-C(=O)-NH-CH2-C(cyclopentyl)-CH2-CH(CO2H)(R,S)- ... -C(=O)-NH-CH(CH=CH-Ph)-CH(Me)-CO2Et; n HCl]

| Example | Y | n | Analysis % (theoretical in brackets) | | |
|---|---|---|---|---|---|
| | | | C | H | N |
| 31 | H | 2 | 56.30 (56.64 | 7.68 7.69 | 8.06 8.81) (a) |
| 32 | COMe | 1 | 58.59 (58.66 | 7.65 7.85 | 8.47 8.55) (b) |
| 33 | SO2Me | 1 | 53.37 (53.52 | 7.09 7.46 | 8.00 8.05) (c) |

(a) ½H2O
(b) H2O
(c) 1½H2O

EXAMPLES 34–39

The compounds of Table 6 were made by the method of Example 30 from the appropriate products from Examples 24–29.

TABLE 6

[Structure: H2N-(CH2)-CH(NHSO2CH3)-C(=O)-NH-CH2-C(cyclopentyl)(CH2-CH(CO2H)-)-C(=O)-NH-CH(CH=CH-Ph)-CH(Me)-CO2R]

| Example | R | Analysis % (theoretical in brackets) | | |
|---|---|---|---|---|
| | | C | H | N |
| 34 | CH2-naphthyl | 60.62 (60.48 | 6.74 6.85 | 6.85 7.05) |
| 35 | indanyl | 59.25 (59.25 | 6.92 7.06 | 7.13 7.27) |
| 36 | CH(Me)-O-C(=O)-Ph | 57.21 (56.88 | 6.75 6.78 | 6.81 6.98) |
| 37 | C11H23 | 60.24 (60.09 | 8.37 8.45 | 6.48 7.01) |

TABLE 6-continued

[Structure: H2N-(CH2)4 chain attached to chiral center with NHSO2CH3, connected via HN to another chiral center with HO2C and CH2 linker to cyclopentyl ring bearing C(=O)NH-CH(iPr with Me)-CH=CH-Ph with CO2R]

| | | Analysis % (theoretical in brackets) | | |
|---|---|---|---|---|
| Example | R | C | H | N |
| 38 | (CH2)4—O-naphthyl | 58.87 (58.79 | 6.90 7.12 | 6.15 6.36) |
| 39 | (CH2)3-cyclohexyl | 59.55 (59.32 | 8.40 7.99 | 7.40 7.28) |

EXAMPLE 40

N-{1-[2(S)-Carboxy-3-(N²-methanesulphonyl-S-lysylamino)-propyl]cyclopentylcarbonyl}-erythro-2-methyl-3-styryl-β-alanine A mixture of the product of Example 30 (0.80 g, 1.15 mmol) and 1M aqueous sodium hydroxide solution (6.9 ml, 6.9 mmol) was stirred at room temperature for 1 hour, then the resulting solution washed with ether (2×5 ml) and loaded onto a column of strongly acidic ion-exchange resin. The column was washed to neutrality using distilled water, then eluted with 5% aqueous pyridine. Evaporation under vacuum of the appropriate fractions gave a glass which was dissolved in distilled water; freeze drying of this aqueous solution provided the required product as a white foam (0.59 g). Found: C,53.64; H,7.59; N,8.42. $C_{29}H_{44}N_4O_8S$; ¼ H2O required C,53.65; H,7.53; N,8.63%.

EXAMPLES 41–43

The compounds of Table 7 were obtained by the general method of Example 40 from the products of Examples 31, 32 and 33 respectively.

TABLE 7

[Structure: NH2-(CH2)4 chain attached to chiral (S) center with XNH, connected via HN to another chiral (S) center with HO2C and CH2 linker to cyclopentyl ring bearing C(=O)NH-CH(S)(Me)-CH=CH-Ph with CO2H]

| | | Analysis % (theoretical in brackets) | | |
|---|---|---|---|---|
| Example | X | C | H | N |
| 41 | H | 57.91 (57.96 | 7.83 8.25 | 9.60 9.66) (a) |
| 42 | COMe | 60.75 (60.53 | 7.80 7.87 | 9.49 9.41) (b) |
| 43 | SO2Me | 53.98 (54.02 | 7.34 7.50 | 9.03 8.69) (c) |

(a) 2¾H2O
(b) 1¼H2O
(c) 2H2O

Preparation 1 cis-3-Methyl-4-styryl-2-azetidinone (Methodology of D. J. Hart et al., J. Org. Chem., 1983, 48, 289)

To a stirred solution of diisopropylamine (1.19 g, 11.9 mmol) in dry tetrahydrofuran (20 ml), at −40° C. under dry nitrogen was added a solution of n-butyllithium in hexane (2.5M; 4.76 ml, 11.9 mmol). The resulting solution was stirred for 0.5 hours, whilst being allowed to warm to room temperature, then cooled to −70° C. before dropwise addition of a solution of ethyl propanoate (1.19 ml, 10 mmol) in dry tetrahydrofuran (20 ml), at such a rate that the temperature did not exceed −65° C. After a further 10 minutes, a solution of N-(trimethylsilyl)cinnamaldimine [prepared by the addition of trans cinnamaldehyde (1.32 g, 10 mmol) to a solution of lithium bis(trimethylsilyl)amide in tetrahydrofuran (1M; 10 ml, 10 mmol) under dry nitrogen at room temperature] was added, again maintaining the internal temperature at <65° C., and stirring was continued for 15 minutes at −70° C. before removal of the cooling bath.

The reaction mixture was stirred for a further 16 hours at room temperature, then diluted with ether (20 ml) and washed successively with 1M hydrochloric acid (3×20 ml), saturated aqueous sodium bicarbonate sodium (25 ml), and saturated brine (20 ml). Evaporation under vacuum of the dried (MgSO4) organic solution gave a brown oil (2.0 g), which was purified by chromatography on silica gel using an ether-hexane elution gradient (1:8–2:1) to give the required product (0.41 g). Found: C,76.64; H,7.10; N,6.97. $C_{12}H_{13}NO$ requires C,76.98; H,7.00; N,7.48%.

Preparations 2–6

The compounds of Table 8 were obtained by the general method of Preparation 1 using the appropriate ethyl ester. In the case of ethyl methoxyacetate the trans β-lactam (Preparation 3) was the major product, in contrast to the other preparations where the cis isomer predominates.

TABLE 8

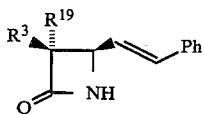

| Preparation | R³ | R¹⁹ | Analysis % (theoretical in brackets) | | |
|---|---|---|---|---|---|
| | | | C | H | N |
| 2 | $CHMe_2$ | H | 77.30 | 7.88 | 6.27 |
| | | | (77.29 | 7.99 | 6.44) (a) |
| 3 | H | OMe | 70.45 | 6.68 | 6.75 |
| | | | (70.92 | 6.45 | 6.89) |
| 4 | OMe | H | 69.66 | 6.46 | 5.96 |
| | | | (69.38 | 6.55 | 6.74) (b) |
| 5 | H | H | 75.91 | 6.54 | 7.03 |
| | | | (75.69 | 6.77 | 7.67) (c) |
| 6 | Me | Me | 77.36 | 7.61 | 6.87 |
| | | | (77.58 | 7.51 | 6.96) |

(a) ½$H_2O$
(b) ½$H_2O$
(c) ½$Et_2O$

Preparation 7 erythro-2-Methyl-3-styryl-β-alanine, methyl ester

A mixture of the product of Preparation 1 (3.8 g, 18.9 mmol) and hydrogen chloride in methanol (2M; 75 ml) was stirred at room temperature for 16 hours, then evaporated under vacuum. The residue was partitioned between ethyl acetate and saturated aqueous sodium bicarbonate solution, then the organic phase separated, dried ($MgSO_4$), and evaporated under vacuum to furnish the required product as a brown oil (3.9 g). Found: C,71.78; H,7.98; N,5.72. $C_{13}H_{17}NO_2$ required, C,71.20; H,7.82; N,6.39%.

Preparations 8-12

The compounds of Table 9 were obtained by the general method of Preparation 7 from the products of Preparations 2-6 respectively.

TABLE 9

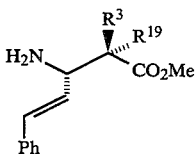

| Compound | R³ | R¹⁹ | Analysis (theoretical in brackets) or TLC data | | |
|---|---|---|---|---|---|
| | | | C | H | N |
| 8 | $CHMe_2$ | H | 71.96 | 8.94 | 5.75 |
| | | | (72.18 | 8.58 | 5.61) (a) |
| 9 | H | OMe | 65.81 | 7.13 | 4.63 |
| | | | (66.36 | 7.28 | 5.95) |
| 10 | OMe | H | 66.07 | 7.08 | 4.98 |
| | | | (66.36 | 7.28 | 5.95) |
| 11 | H | H | Rf 0.1 (silica; ethyl acetate) | | |
| 12 | Me | Me | 72.07 | 8.28 | 5.77 |
| | | | (72.07 | 8.21 | 6.00) |

(a) ½$H_2O$

We claim:
1. A compound of the formula (I):

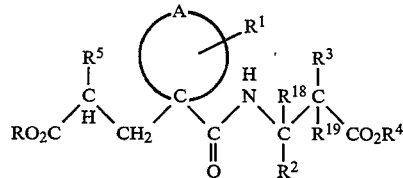

or the pharmaceutically acceptable salt thereof, wherein A completes a 4 to 7 membered carbocyclic ring which may be saturated or monounsaturated and which may optionally be fused to a further saturated or unsaturated 5 or 6 membered carbocyclic ring; each of R and $R^4$ is independently H, $C_1$-$C_6$ alkyl, benzyl or a biolabile ester-forming group other than $C_1$-$C_6$ alkyl or benzyl, said ester-forming group being selected from undecyl, 1-(2,2-diethylbutyryloxy)ethyl, 2-ethylpropionyloxymethyl, 1-(2-ethylpropionyloxy)ethyl, 1-(2,4-dimethylbenzoxy)ethyl, 1-(benzyloxy)benzyl, 1-benzoxyethyl, 4-(1-naphthyloxy)butyl, 2-methyl-1-propionoxypropyl, 2,4,6-trimethylbenzoyloxymethyl, 1-(2,4,6-trimethylbenzyloxy)ethyl, pivaloyloxymethyl, phenethyl, phenpropyl, 1-naphthylmethyl, 3-(cyclohexyl)propyl, 2,2,2-trifluoroethyl, naphthyl, 2,4-dimethylphenyl, 4-(tert.-butyl)phenyl, 5-(4-methyl-1,3-dioxalynyl-2-onyl)-methyl and 5-indanyl;

$R^1$ is H or $C_1$-$C_4$ alkyl;

$R^2$ and $R^{18}$ are each independently selected from H and aryl($C_2$-$C_4$)alkenyl; or $R^3$ and $R^{19}$ are each independently selected from H, $C_1$-$C_4$ alkyl and ($C_1$-$C_4$)alkoxy;

with the proviso that one of $R^2$ and $R^{18}$ must be H and the other must be aryl($C_2$-$C_4$)alkenyl, and at least one of $R^3$ and $R^{19}$ must always be H; and $R^5$ is $C_1$-$C_6$ alkyl, $C_2$-$C_6$ alkenyl, $C_2$-$C_6$ alkynyl, $C_3$-$C_7$ cycloalkyl or $C_7$ cycloalkenyl; or $R^5$ is a $C_1$-$C_6$ alkyl substituted by halo, hydroxy, $C_1$-$C_6$ alkoxy, $C_1$-$C_6$ alkoxy, $C_3$-$C_7$ cycloalkyl, $C_7$ cycloalkenyl, aryl, aryloxy, heterocyclyl, —$NR^6R^7$, —$NR^8$—$COR^9$, —$NR^8SO_2R^{10}$, —$CONR^7R^7$ or $R^6R^7N$—($C_1$-$C_6$)alkoxy; or $R^5$ is $C_1$-$C_6$ alkyl substituted by a group of the formula:

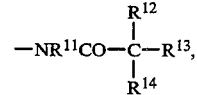

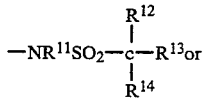

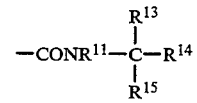

wherein $R^6$ and $R^7$ are each independently H, $C_1$-$C_4$ alkyl, $C_3$-$C_7$ cycloalkyl, aryl, aryl($C_1$-$C_4$)alkyl, $C_2$-$C_6$ alkoxyalkyl, or heterocyclyl; or the two groups $R^6$ and $R^7$ are taken together with the nitrogen to which they are attached to form a pyrrolidinyl, piperidino, morpholino, piperazinyl and N-($C_1$–$C_4$)alkyl-piperazinyl group;

or $R^5$ is a biolabile mono or di-ester derivative of S-lysylaminomethyl, $N^2$-acetyl acetyl-S-lysylaminomethyl or $N^2$-methanesulphonyl-S-lysylaminomethyl, wherein the ester-forming group of said derivative is as previously defined for R and $R^4$ when at least one of said R and $R^4$ is other than H;

$R^8$ is H or $C_1$–$C_4$ alkyl;

$R^9$ is $C_1$–$C_4$ alkyl, $CF_3$, aryl, aryl($C_1$–$C_4$)alkyl, aryl(-$C_1$–$C_4$)alkoxy, heterocyclyl, $C_1$–$C_4$ alkoxy or $NR^6R^7$ wherein $R^6$ and $R^7$ are as previously defined;

$R^{10}$ is $C_1$–$C_4$ alkyl, $C_3$–$C_7$ cycloalkyl, aryl or heterocyclyl;

$R^{11}$ is H, $C_1$–$C_6$ alkyl, aryl or $C_3$–$C_7$ cycloalkyl;

$R^{12}$ is $R^{11}CONR^{11}$—, $R^{16}R^{17}N$-$(CH_2)_p$— or $R^{11}O$—, wherein each $R^{11}$ is as previously defined above;

$R^{13}$ and $R^{14}$ are each independently H or $C_1$–$C_6$ alkyl; or $R^{13}$ is H and $R^{14}$ is $C_1$–$C_6$ alkyl which is substituted by OH, $C_1$–$C_4$ alkoxy, SH, $SCH_3$, $NH_2$, aryl($C_1$–$C_6$)alkyl OCONH—, $NH_2CO$—, $CO_2H$, guanidino, aryl or heterocyclyl; or the two groups $R^{13}$ and $R^{14}$ are joined together to form, with the carbon atom to which they are attached, a 5 or 6 membered carbocyclic ring which may be saturated or monounsaturated and which may optionally be substituted by $C_1$–$C_4$ alkyl or fused to a further 5 or 6 membered saturated or unsaturated carbocyclic ring; or $R^{13}$ is H, and $R^{12}$ and $R^{14}$ are joined together to form, with the carbon atom to which they are attached, a 5 or 6 membered carbocyclic ring which may be saturated or monounsaturated and which may optionally by substituted by $C_1$–$C_4$ alkyl or used to a further 5 or 6 membered saturated or unsaturated carbocyclic ring; or $R^{13}$ is H, and $R^{12}$ and $R^{14}$ are linked to form a 2-(N—$COR^{11}$-4-aminopyrrolidinyl) group;

$R^{15}$ is $R^{16}R^{17}NCO$—, $R^{11}OCH_2$— or heterocyclyl, wherein $R^{11}$ is as previously defined above;

$R^{16}$ is $R^{17}$ are each independently H or $C_1$–$C_4$ alkyl, and p is 0 or an integer of from 1 to 6; or the pharmaceutically acceptable salts thereof.

2. A compound according to claim 1, wherein A is $(CH_2)_4$ and $R^1$ is H.

3. A compound according to claim 2, wherein $R^2$ and $R^{18}$ are each independently selected from H and styryl, and $R^3$ and $R^{19}$ are each independently selected from $H_1$ $C_1$–$C_3$ alkyl and methoxy.

4. A compound according to claim 3, in which $R^2$ is styryl, $R^{18}$ is H and one of $R^3$ and $R^{19}$ is H and the other of $R^3$ and $R^{19}$ is methyl, methoxy or isopropyl.

5. A compound according to claim 2, in which $R^5$ is methylene substituted by a group of formula —NHCO$CR^{12}R^{13}R^{14}$ in which $R^{12}$ is $NH_2$, $R^{11}CONH$— or $R^{11}SO_2NH$—, $R^{13}$ is H and $R^{14}$ is —$(CH_2)_4NH_2$.

6. A compound according to claim 5, in which $R^5$ is $N^2$-acetyl-S-lysylaminomethyl, $N^2$-methanesulphonyl-S-lysyl-aminomethyl, $N^2$-phenylsulphonyl-S-lysyl-aminomethyl, $N^2$-t-butoxycarbonyl-S-lysylaminomethyl or S-lysyl-aminomethyl.

7. A compound according to claim 2, in which $R^5$ is $C_1$–$C_6$ alkyl substituted by $C_1$–$C_6$ alkoxy or by $C_1$–$C_6$ alkoxy($C_2$–$C_6$)alkoxy.

8. A compound according to claim 1, in which one or both of R and $R^4$ is an ethyl, benzyl, 1-(2,2-diethylbutyryloxy)-ethyl, 2-ethylpropionyloxymethyl, 1-(2-ethylpropionyloxy)ethyl, 1-(2,4-dimethylbenzoxy)ethyl, 1-(benzyloxy)benzyl, 1-(benzoxy)ethyl, 2-methyl-1-propionoxy-propyl, 2,4,6-trimethylbenzoyloxymethyl, 1-(2,4,6-trimethyl-benzyloxy)-ethyl, pivaloyloxymethyl, phenethyl, phenpropyl, 2,2,2-trifluoroethyl, 1- or 2-naphthyl, 2,4-dimethylphenyl, 4-t-butylphenyl, 5-(4-methyl-1,3-dioxalynyl-2-onyl)methyl or 5-indanyl group.

9. A compound according to claim 1, in which R,$R^1$ and $R^4$ are each H, A is $(CH_2)_4$, $R^2$ is styryl, $R^3$ is methyl, $R^2$ and $R^3$ being in the erythro-relative configuration, $R^{18}$ and $R^{19}$ are H, and $R^5$ is S-lysylaminomethyl, $N^2$-acetyl acetyl-S-lysylaminomethyl or $N^2$-methanesulphonyl-S-lysylaminomethyl, or a biolabile mono or di-ester derivative as previously defined in claim 1.

10. A compound according to claim 2, in which $R^5$ is an unsubstituted $C_1$–$C_6$ alkyl group.

11. A compound according to claim 3, in which $R^2$ is styryl, $R^{18}$ is H, and $R^3$ and $R^{19}$ is methyl or methoxy.

12. A compound according to claim 11, in which $R^3$ is methyl or methoxy and $R^{19}$ is H.

13. A compound according to claim 1, in which R, $R^1$ and $R^4$ are each H, A is $(CH_2)_4$, $R^2$ is styryl, $R^3$ is H, methyl or methoxy, with $R^2$ and $R^3$ being in the erythro-relative configuration, $R^{18}$ and $R^{19}$ are both H, and $R^5$ is n-propyl, or a biolabile mono or di-ester derivative as previously defined in claim 1.

14. A pharmaceutical composition comprising a compound of the formula (I) as claimed in claim 1, or a pharmaceutically acceptable salt thereof, together a pharmaceutically acceptable diluent or carrier.

15. A method of eliciting diuretic activity in a patent afflicted with a cardiovascular disorder caused by the lack of such activity, which comprises administering to said patient an effective amount of a compound of the formula (I), or a pharmaceutically acceptable salt thereof, as claimed in claim 1.

* * * * *